United States Patent
Gael et al.

(10) Patent No.: US 6,203,496 B1
(45) Date of Patent: Mar. 20, 2001

(54) APPARATUS WITH REAGENTS FOR DETECTION OF MEDICAL CONDITIONS

(76) Inventors: Michael R. Gael, 2004 Faymont Ave., Manhattan Beach, CA (US) 90266; Sidney Gael, 11628 Montana Ave., Los Angeles, CA (US) 90049; William Gael, 1225 River Rd., #4D, Edgewater, NJ (US) 07020

( * ) Notice: Subject to any disclaimer, the term of this patent is extended or adjusted under 35 U.S.C. 154(b) by 0 days.

(21) Appl. No.: 09/372,876

(22) Filed: Aug. 12, 1999

(51) Int. Cl.[7] .................................................. A61B 5/00
(52) U.S. Cl. .................. 600/362; 600/573; 600/584; 604/358; 604/362
(58) Field of Search .................................. 600/362, 573, 600/584, 309; 602/52; 604/358, 362

(56) References Cited

U.S. PATENT DOCUMENTS

| | | |
|---|---|---|
| 2,156,880 | 5/1939 | Slomon . |
| 4,666,833 | 5/1987 | Roy et al. . |
| 4,724,204 | 2/1988 | Steinbach et al. . |
| 5,181,905 | 1/1993 | Flam . |
| 5,217,444 | 6/1993 | Schoenfeld . |
| 5,267,989 | * 12/1993 | Moyet-Ortiz ................. 600/573 X |
| 5,445,147 | * 8/1995 | Schoendorfer et al. ............ 600/362 |
| 5,525,346 | 6/1996 | Hartung et al. . |
| 5,529,782 | 6/1996 | Staab . |
| 5,766,212 | 6/1998 | Jitoe et al. . |
| 5,817,012 | * 10/1998 | Schoendorfer .................. 600/573 X |
| 5,823,953 | 10/1998 | Roskin et al. . |
| 6,042,543 | * 3/2000 | Warwick et al. .................... 600/362 |

FOREIGN PATENT DOCUMENTS

1355018 A 41   2/1964   (FR) .

* cited by examiner

*Primary Examiner*—Cary O'Connor
*Assistant Examiner*—Ryan Carter
(74) *Attorney, Agent, or Firm*—Knobbe Martens Olson and Bear, LLP

(57) ABSTRACT

Disclosed is a disposable diaper that has one or more chemical reagents provided in the absorbent region of the diaper, which comes into contact with urine when a patient wearing the diaper urinates. These chemical reagents change color when they contact urine containing abnormal levels of substances, such as leukocytes, blood, glucose, nitrites, protein, ketones, bilirubin, or urobilinogen; which substances may indicate the presence of a medical abnormality. Such a color change provides a visible indication of an abnormality in the urine and thus a possible incipient medical condition, such as a urinary tract infection, diabetes mellitus, hematuria, or the like. Such a color change is easily assessed by personnel having limited medical training, allowing such personnel to screen patients for these medical conditions and refer them to the appropriate medical personnel.

33 Claims, 5 Drawing Sheets

APPARATUS WITH REAGENTS FOR DETECTION OF MEDICAL CONDITIONS

BACKGROUND OF THE INVENTION

1. Field of the Invention

This invention relates to the detection of a variety of medical conditions, and more particularly to a method and apparatus for the detection and monitoring of urinary tract infections and other medical conditions by personnel with limited medical training.

2. Description of the Related Art

The medical care of elderly or incontinent adults, especially those confined to long-term care institutions such as nursing homes, presents a variety of difficulties. Such individuals are generally in a relatively poor state of health and are often unable to communicate effectively with their caregivers. In addition, the personnel assigned to the care of such patients are often overworked and have limited medical training. In these circumstances, medical conditions such as diabetes mellitus or biliary obstruction often go unnoticed until they have become serious and often life-threatening. Urinary tract infections present a particularly difficult problem. Such infections often go unnoticed in nursing care facilities until the patients are hypotensive due to septic shock, and even if such patients are promptly taken to an emergency room, it is often too late to rescue them due to their generally poor state of health and the advanced state of the infection. Thousands of such patients die every year in this manner. It is thus highly desirable to detect incipient urinary tract infections at an early stage, so as to intervene before the condition of such patients becomes grave. However, the symptoms of early-stage urinary tract infections are not easily assessable if the patient himself does not communicate with the caregiver. Also, the limited time devoted to such patients by caregivers who often have limited medical training makes such intervention difficult. It is thus highly desirable to develop a method whereby personnel with limited training can easily detect and monitor these patients for such infections.

However, a simple method of doing this has not yet been developed. Methods are known, for example, for using external apparatuses for detecting the pH of vaginal secretions (U.S. Pat. No. 5,823,953 to Roskin, et al.) and for detecting the presence of bed sores beneath dressings (U.S. Pat. No. 5,181,905 to Flam). However, a simple, effective, and reliable method of easily detecting medical conditions such as urinary tract infections in long-term care residents who may be noncommunicative has not yet been developed.

SUMMARY OF THE INVENTION

It is, accordingly, an object of this invention to provide a method and apparatus for detecting and monitoring medical conditions such as urinary tract infections, hematuria, and diabetes mellitus in mammals, particularly adult humans, and more particularly geriatric patients. Such method and apparatus may be safely and reliably employed in a short period of time even by personnel having limited medical training.

The present invention thus relates to a disposable apparatus, such as a diaper, pad, napkin, panty liner, or the like, having chemical reagents provided in the absorbent material in a region of the apparatus which comes into contact with urine when a patient wearing the apparatus urinates. These chemical reagents are well known to change color when they come in contact with urine containing abnormal levels of a substance, such as leukocytes, blood, glucose, nitrites, protein, ketones, bilirubin, or urobilinogen, or abnormal pH or specific gravity, which may indicate the presence of one or more medical abnormalities. One or more of these chemical reagents are provided in the appropriate area of the absorbent material of the apparatus during the process of manufacture of the apparatus. The chemical reagents change color when they come into contact with urine containing the one or more of the substances described above. Such a color change provides an easily visible indication of an abnormality in the urine and thus a possible incipient medical condition. Such a color change is easily assessed even by personnel having limited medical training, allowing such personnel to screen the patients in the facility and direct the attention of the trained medical personnel to those patients most likely to require attention, thus making the medical care of such patients more efficacious. In addition, because the diapers or other underclothing of such patients must be changed at regular intervals by caregivers as a part of the routine care of such patients, the assessment of such incipient medical conditions does not involve additional time-consuming steps, but rather simply involves the caregiver glancing at the inside of such diapers or underclothing as they remove them from the patients.

These and other objects, features, and advantages of the invention will become more apparent when the detailed description is studied in conjunction with the drawings, in which like reference characters indicate like elements in the various figures.

DETAILED DESCRIPTION OF THE PREFERRED EMBODIMENTS

It is an object of this invention to provide a method and apparatus for detecting and monitoring medical conditions such as urinary tract infections, hematuria, and diabetes mellitus in mammals, particularly humans, and more particularly adult humans. The present invention has great utility in, for example, geriatric patients (i.e., those persons over the age of 65) who may be incontinent of urine.

Figure 1:
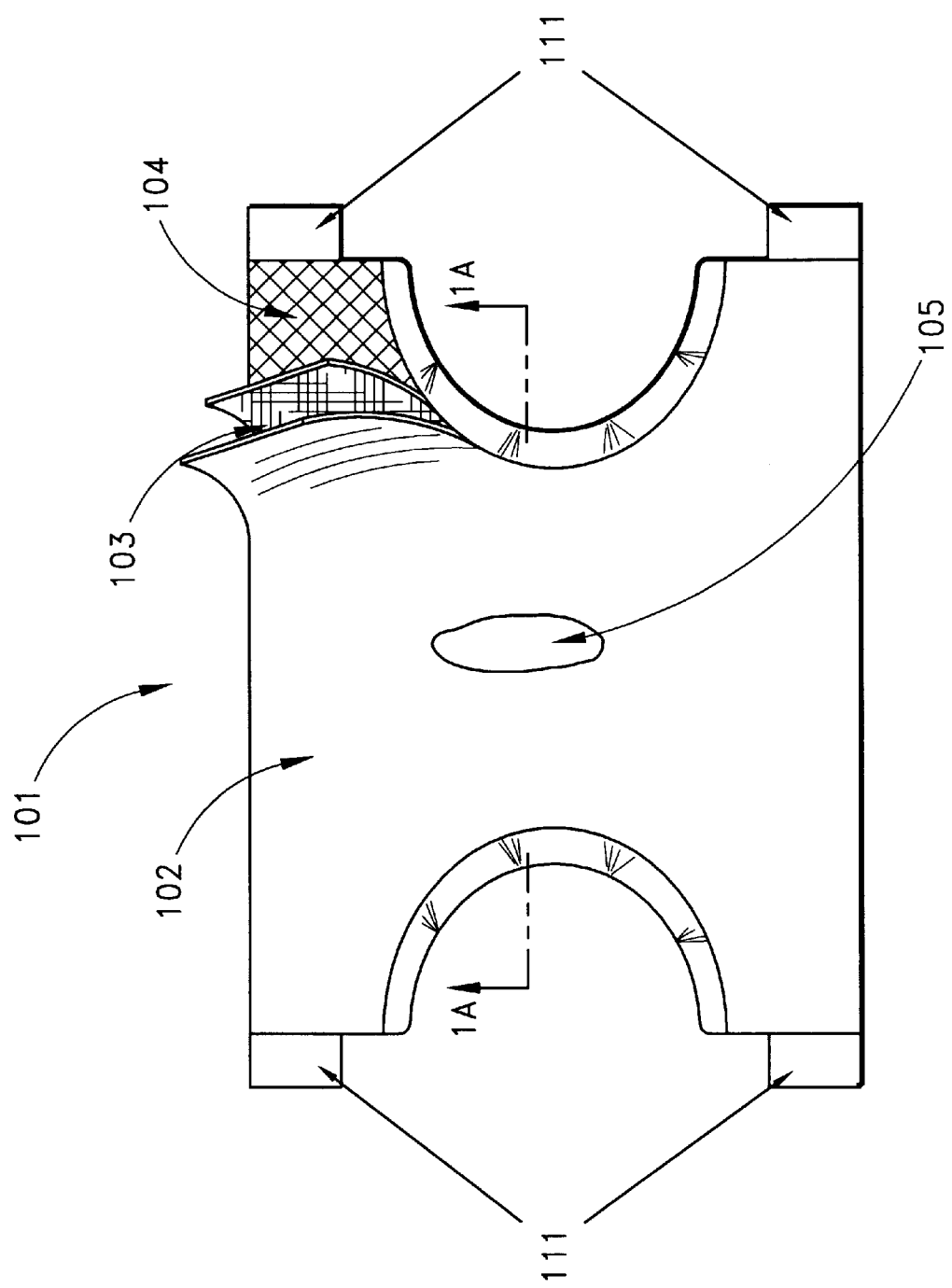
FIG. 1 is a top view showing a diaper in accordance with an embodiment of the present invention.

FIG. 1 shows a diaper 101 which is a first embodiment of the present invention. The diaper 101 may be a disposable diaper of the type in common use or may be a diaper in which the liquid-absorbent layer 103 is specially adapted for the purpose. The diaper comprises a liquid-permeable inside sheet 102, a liquid-absorbent layer 103, and a liquid-impermeable outside sheet 104. The diaper may be fastened by methods commonly known in the art, such as adhesive tape; hook-and-eyelet fasteners, such as those sold under the trademarked name Velcro™; hooks; pins; or the like. FIG. 1 depicts a diaper 101 with adhesive tape tabs 111. The liquid-absorbent layer 103 comprises paper, cloth, or other fibers in common use which have liquid absorbing properties. At least one chemical reagent is provided in the liquid-absorbent layer 103; examples thereof include glucose oxidase, at a concentration of about 16.3% by weight (this may be obtained from, for example, the fungus *Aspergillus niger*); peroxidase, at a concentration of about 0.6% by weight; potassium iodide, at a concentration of about 7.0% by weight; cumene-hydroperoxide tetramethylbenzidine (this is preferably cumene-hydroperoxide 3,3',5,5', tetramethylbenzidine, although other methyl group substitution configurations may be possible), at a concentration of about 22.5% by weight; naphthyl ester, at a concentration of about 0.4% by weight; diazonium salt, at a concentration of about 0.2% by weight; arsenilic acid tetrahydrobenzo (h) quinolin (this is preferably p-arsenilic acid 1, 2, 3, 4 tetrahydrobenzo (h) quinolin, although other substitution configurations may be possible), at a concentration of about 1.4% by weight; methyl red, at a concentration of about 0.2% by weight; bromthymol blue, at a concentration of about 2.8% by weight; tetrabromphenol blue, at a concentration of about 0.3% by weight; sodium nitroprusside, at a concentration of about 7.1% by weight; dichloroaniline diazonium salt (this is preferably 2, 4-dichloroaniline diazonium salt, although other substitution configurations may be possible), at a concentration of about 0.4% by weight; diethylaminobenzaldehyde (this is preferably p-diethylaminobenzaldehyde, although other substitution configurations may be possible), at a concentration of about 2.9% by weight; and polyacid, at a concentration of about 1.2% by weight. It should be understood that other concentrations of these or similar reagents may also be employed. These reagents, the substances with which they react, and the color changes associated with these reactions are listed in Table 1.

The chemical regents may be provided in the liquid-absorbent layer by any of a number of methods commonly known in the art. Examples thereof include the application of powder in appropriate areas of the liquid-absorbent layer, the weaving of fibers impregnated with the appropriate reagents in the appropriate areas of the liquid-absorbent layer, and the like. These reagents can be provided during the manufacturing process of the diaper in the liquid-absorbent layer in the crotch area between the inside sheet (the sheet next to the skin) of the diaper and the liquid-absorbent layer in such a manner that color changes associated with the various reactions are easily visible through the inside sheet on removal of the diaper, or through the outside sheet even before removal of the diaper. A change in the color of any of the reagents indicates the presence of an abnormal substance in the urine, and a possible medical abnormality.

Figure 1A:
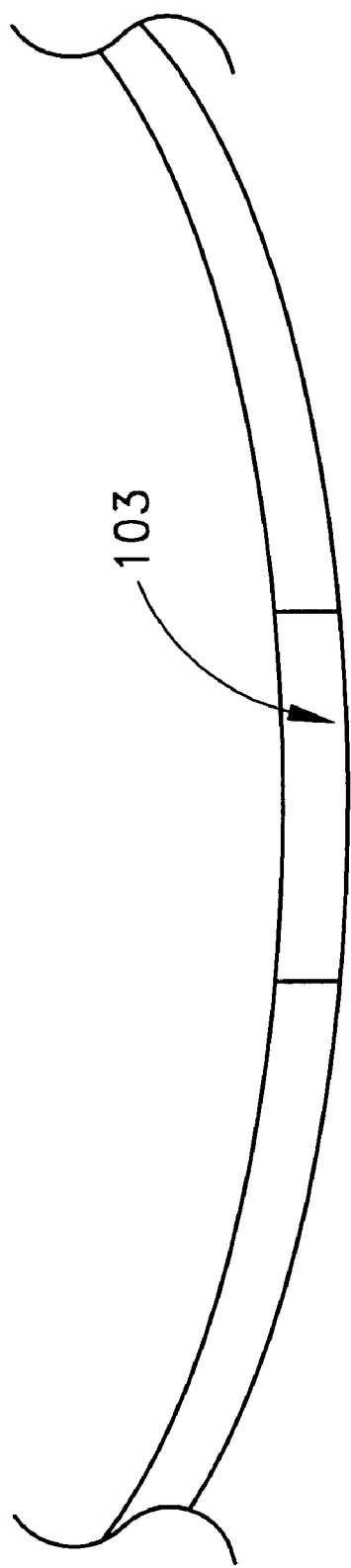
FIG. 1A is a cross-sectional view taken along the line A—A in FIG. 1.
Figure 2:
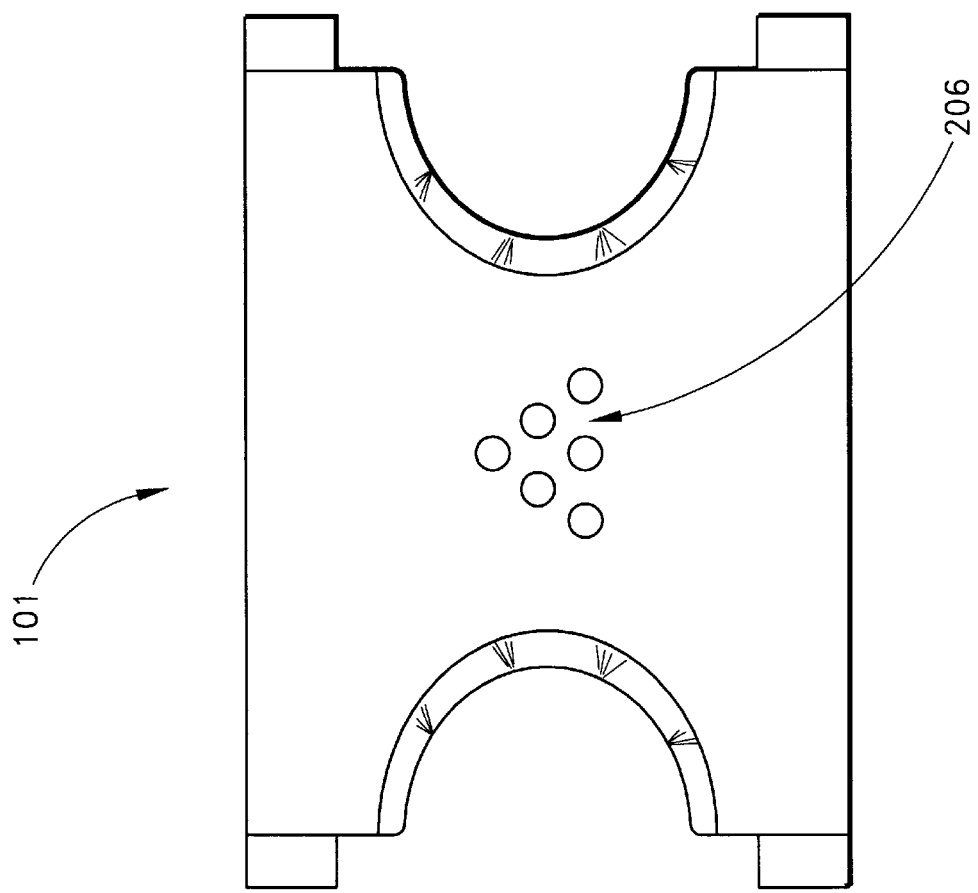
FIG. 2 is a top view showing a diaper in accordance with another embodiment of the present invention.

A single reagent may be provided in the liquid-absorbent layer in the region 105 indicated in FIG. 1, facilitating the detection of a single substance whose presence or concentration is abnormal. The region 105 lies within the liquid-absorbent layer 103, as shown in FIG. 1A. Alternatively, a number of reagents may be provided in the liquid-absorbent layer in the form of the array 206 having, for example, the unique pattern shown in FIG. 2, so as to facilitate the detection of abnormal levels of a number of substances. The pattern of this array 206 may be such as to make the orientation in which the diaper should be viewed unmistakable, such as the triangular pattern shown in FIG. 2. This asymmetrical pattern makes it easy for personnel with limited training to hold the diaper in the proper orientation when viewing the color changes. Such personnel will thus have to receive only very limited training, perhaps in the form of a portable color chart (not shown in the figures) for rapid comparison with the colors present on diapers removed from patients. It should be noted, however, that a color chart will often be unnecessary in certain embodiments of the present invention. Any color change can be reported by medical personnel to a physician.

Figure 3:
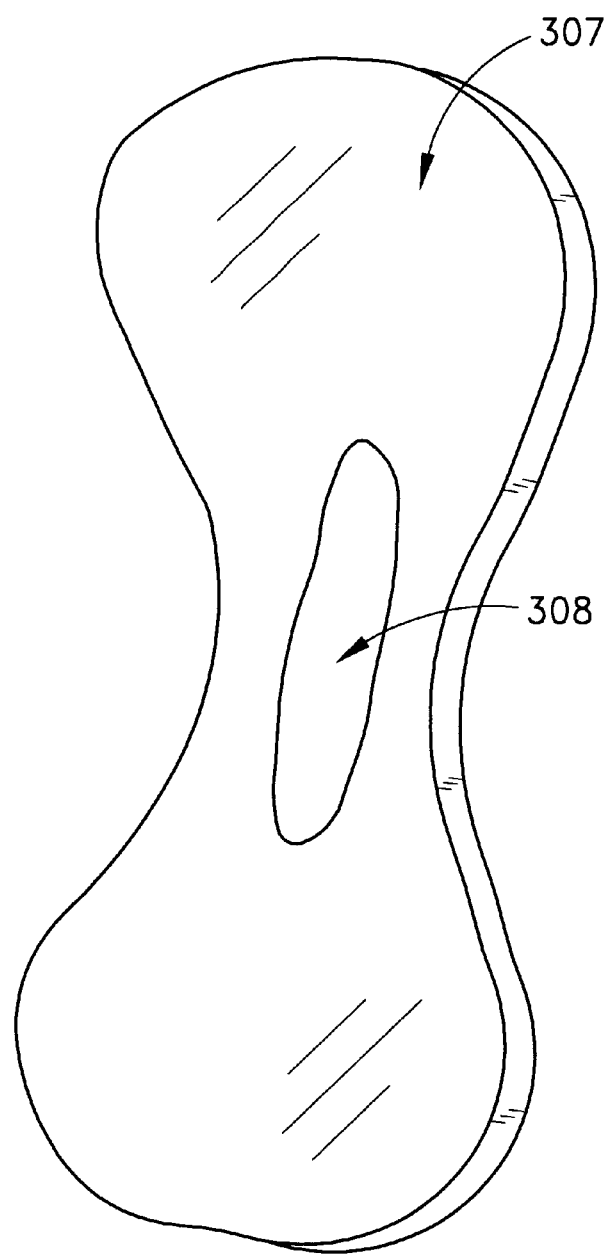
FIG. 3 is a top view showing a pad in accordance with another embodiment of the present invention.

A second embodiment of the invention is shown in FIG. 3. This figure depicts a panty liner 307 having a structure similar to that of the diaper 101 and designed to be worn in the same general manner. The panty liner 307 is of a type commonly known in the art with respect to the shape thereof The liquid-absorbent layer of the panty liner 307 also has a region 308 which contains at least one reagent which changes color when it comes into contact with abnormal levels of certain substances in urine. Any of the reagents listed in Table 1 may be employed as this reagent. Although FIG. 3 depicts a panty liner having only a single region 308 impregnated with a single reagent, it should be understood that an array of a number of reagents such as array 206 in FIG. 2 may also be employed in panty liner 307.

Figure 4:
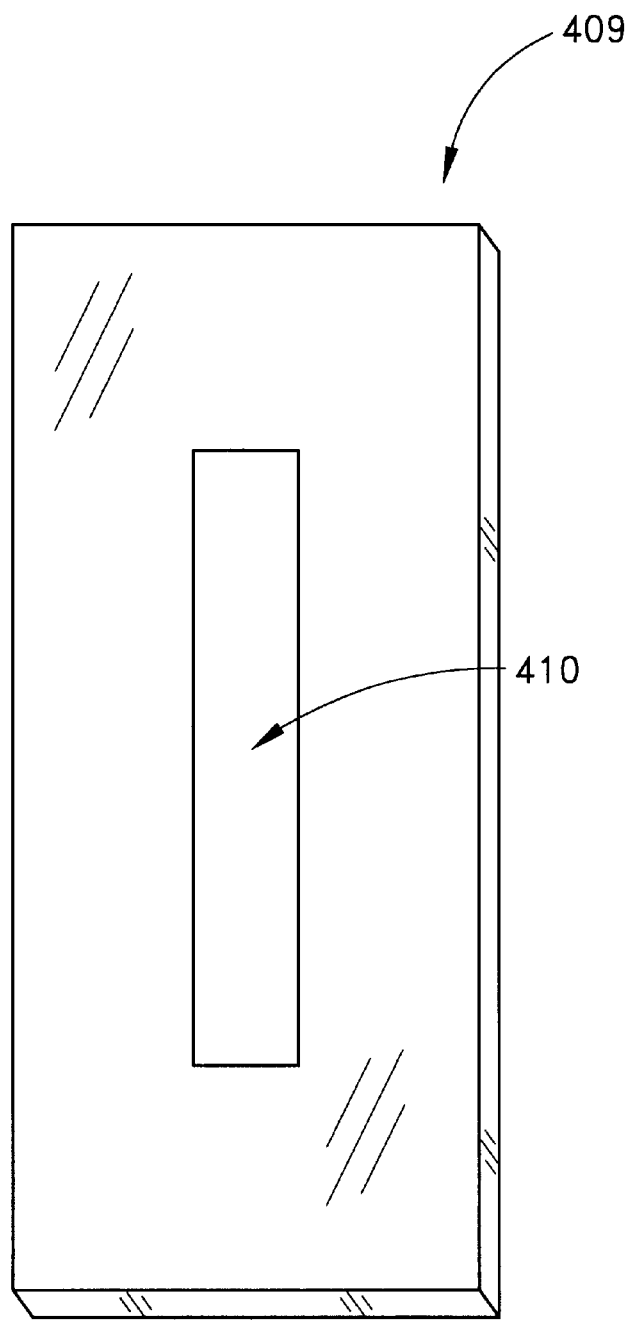
FIG. 4 is a top view showing a panty liner in accordance with another embodiment of the present invention.

A third embodiment of the invention is shown in FIG. 4. This figure depicts a pad 409 having a structure similar to that of the diaper 101 and designed to be worn in the same general manner. The pad 409 is of a type commonly known in the art with respect to the shape thereof; the term "pad" here includes napkins and similar apparatuses. The liquid-absorbent layer of the pad 409 also has a region 410 which contains at least one reagent which changes color when it comes into contact with certain substances in urine. Any of the reagents listed in Table 1 may be employed as this reagent. Although FIG. 4 depicts a pad having only a single region 410 impregnated with a single reagent, it should be understood that an array of a number of reagents such as array 206 in FIG. 2 may also be employed in pad 409.

Providing these reagents in the liquid-absorbent layer in the manner described above allows personnel with limited medical training to screen patients for such conditions as urinary tract infections, glycosuria from diabetes mellitus or other causes of hyperglycemia, hematuria, and kidney or biliary abnormalities, among others. This screening may be accomplished quickly and easily during the course of normal patient care.

As used herein, "glycosuria" is defined as the presence of glucose in urine. "Biliary abnormality" is defined as any inflammatory, fibrotic, or obstructive disorder of the liver, bile ducts, or pancreas that produces elevation in serum total, direct, or indirect bilirubin levels; including, for example, cholelithiasis, cholecystitis, Gilbert's disease, hepatic cancer, cholangiocarcinoma, pancreatic cancer, and hepatitis. When serum bilirubin concentrations are elevated, bilirubin can appear in the urine, as can urobilinogen. "Ketonuria" is defined as the presence of ketones (ketone bodies), for example beta hydroxybutyrate, in urine. "Proteinuria" is defined as the presence of protein, for example albumin, in urine. "Hematuria" is defined as the presence of red blood cells present in urine, not simply those amounts considered clinically significant.

The presence of glucose in urine is abnormal and generally reflects a blood glucose concentration of more than 240 mg/dl, the approximate concentration at which renal tubular glucose transport carrier proteins become saturated. Hence, higher blood glucose concentrations result in glucose "spilling over" from the blood into the urine, and the detection of urinary glucose thus provides a detection mechanism for the elevated blood glucose that is characteristic of diabetes mellitus. Other causes of hyperglycemia that can produce glycosuria include corticosteroid administration, glucagonoma, and others.

While we have shown and described certain preferred embodiments, it is understood that the invention may be embodied otherwise than as herein specifically illustrated and described. Other embodiments that are apparent to those of ordinary skill in the art are also within the scope of the invention. Accordingly, the scope of the present invention is not intended to be limited by the foregoing, but rather by reference to the appended claims.

TABLE 1

| Substance | Reagent | Abnormal Color Changes | | |
|---|---|---|---|---|
| | | Low | Medium | High |
| Glucose | 16.3% Glucose Oxidase 0.6% Peroxidase (peroxidase) 7.0% Potassium iodide | Khaki | Brown | Dark Brown |
| Blood | 22.5% Cumene-hydroperoxide 3,3' 5,5' tetramethyl-benzidine | Lt. Green | Med. Green | Dark Blue |
| Leukocytes | .04% Naphthyl ester 0.2% Diazonium salt | Beige/Pink | Lavender | Purple |
| Nitrite | 1.4% p-Arsanilic (arsenilic) acid 1,2,3,4 Tetrahydrobenzo (h) quinolin | Lt. Pink | Med. Pink | Pink |
| pH | 0.2% Methyl red 2.8% Bromthymol blue | Orange/Yellow | Lt. Green | Green/Blue |
| Protein | 0.3% Tetrabromphenol blue | Yellow/Green | Green | Green-Blue |
| Ketone | 7.1% Sodium nitroprusside | Pink | Purple | Deep Purple |
| Bilirubin | 0.4% 2,4-dichloroaniline diazonium salt | Cream Pink | Beige Pink | Lavender Pink |
| Urobilinogen | 2.9% p-diethylamino-benzaldehyde | Pink | Deeper Pink | Deepest Pink |
| Specific Gravity | 2.8% Bromthymol blue 1.2% polyacid | Blue | Blue Green | Khaki-Yellow |

What is claimed is:

1. A method for detecting and monitoring a medical condition in a mammal, comprising the steps of:
    positioning an absorbent apparatus on the mammal so as to receive urine from the mammal, the apparatus having at least one reagent configured to indicate, by a visual color change, the presence of the medical condition, wherein the medical condition is selected from the group consisting of (a) urinary tract infection, (b) hematuria, (c) glycosuria, (d) biliary abnormality, (e) ketonuria, and (f) proteinuria; and
    determining from the color of the reagent whether an abnormal level of a substance indicating the presence of said medical condition is present in the urine received on the apparatus.

2. The method of claim 1, wherein the apparatus is a diaper.

3. The method of claim 1, wherein the apparatus is a panty liner.

4. The method of claim 1, wherein the apparatus is a pad.

5. The method of claim 1, wherein said medical condition is a urinary tract infection.

6. The method of claim 5, wherein said substance is selected from the group consisting of leukocytes and nitrites.

7. The method of claim 5, wherein the reagent is selected from the group consisting of naphthyl ester, diazonium salt, arsenilic acid, and tetrahydrobenzo (h) quinolin.

8. The method of claim 1, wherein said medical condition is hematuria, and said substance is red blood cells.

9. The method of claim 8, wherein the reagent is cumene-hydroperoxide tetramethylbenzidine.

10. The method of claim 1, wherein said medical condition is glycosuria and said substance is glucose.

11. The method of claim 10, wherein the reagent is selected from the group consisting of glucose oxidase, peroxidase, and potassium iodide.

12. The method of claim 1, wherein the condition is proteinuria and the substance is a protein.

13. The method of claim 12, wherein the reagent is tetrabromphenol blue.

14. The method of claim 1, wherein the medical condition is ketonuria and the substance is ketones.

15. The method of claim 14, wherein the reagent is sodium nitroprusside.

16. The method of claim 1, wherein the medical condition is a biliary abnormality and the substance is selected from the group consisting of bilirubin and urobilinogen.

17. The method of claim 16, wherein the reagent is selected from the group consisting of dichloroaniline diazonium salt and diethylaminobenzaldehyde.

18. A method for detecting and monitoring a medical condition in an adult mammal, comprising the steps of:
    positioning an absorbent apparatus on the mammal so as to receive urine from the mammal, the apparatus having at least one reagent configured to indicate, by a visual color change, the presence of the medical condition when in contact with urine;
    collecting urine on the apparatus such that the urine contacts the reagent;
    determining from the color of the reagent whether an abnormal level of a substance indicating the presence of said medical condition is present in the urine received on the apparatus.

19. The method of claim 18, wherein the apparatus is a diaper.

20. The method of claim 18, wherein the apparatus is a panty liner.

21. The method of claim 18, wherein the apparatus is a pad.

22. An apparatus for determining the presence of a medical condition in a mammal, said apparatus configured to be positioned on the mammal to receive urine from the mammal, said apparatus comprising:
- a liquid-impermeable outside sheet;
- a liquid-absorbent layer;
- at least one reagent on or in said liquid-absorbent layer, said reagent being configured to detect, in urine, an abnormal level of a substance associated with a medical abnormality after said reagent contacts said urine, said detection occurring by a visible color change, said medical condition being selected from the group consisting of: (a) urinary tract infection, (b) hematuria, (c) glycosuria, (d) biliary abnormality, (e) ketonuria, and (f) proteinuria.

23. The apparatus of claim 22, wherein the liquid-absorbent layer further comprises paper.

24. The apparatus of claim 22, wherein the liquid-absorbent layer further comprises cloth.

25. The apparatus of claim 22, wherein the apparatus is a diaper.

26. The apparatus of claim 22, wherein the apparatus is a panty liner.

27. The apparatus of claim 22, wherein the apparatus is a pad.

28. The apparatus of claim 22, wherein said medical condition is a urinary tract infection, and wherein the reagent is selected from the group consisting of naphthyl ester, diazonium salt, arsenilic acid, and tetrahydrobenzo (h) quinolin.

29. The apparatus of claim 22, wherein said medical condition is hematuria, and the reagent is cumene-hydroperoxide tetramethylbenzidine.

30. The apparatus of claim 22, wherein said medical condition is glycosuria and the reagent is selected from the group consisting of glucose oxidase, peroxidase, and potassium iodide.

31. The apparatus of claim 22, wherein the condition is proteinuria and the reagent is tetrabromphenol blue.

32. The apparatus of claim 22, wherein the medical condition is ketonuria and the reagent is sodium nitroprusside.

33. The apparatus of claim 22, wherein the medical condition is a biliary abnormality and the reagent is selected from the group consisting of dichloroaniline diazonium salt and diethylaminobenzaldehyde.

\* \* \* \* \*